US00PP10048P

United States Patent [19]

Trees

[11] Patent Number: Plant 10,048

[45] Date of Patent: Sep. 30, 1997

[54] NEW GUINEA IMPATIENS NAMED 'ORANGE CRUSH'

[75] Inventor: Scott C. Trees, Arroyo Grande, Calif.

[73] Assignee: Ball Horticultural Company, West Chicago, Ill.

[21] Appl. No.: 685,674

[22] Filed: Jul. 24, 1996

[51] Int. Cl.[6] ..... A01H 5/00

[52] U.S. Cl. ..... Plt./87.6

[58] Field of Search ..... Plt./87.6

*Primary Examiner*—James R. Feyrer

*Attorney, Agent, or Firm*—Burns, Doane, Swecker & Mathis, L.L.P.

[57] ABSTRACT

A new and distinct New Guinea Impatiens cultivar named 'Orange Crush' is provided. This new cultivar was the result of a controlled breeding program wherein a plant designated '305' (non-patented in the United States) was pollinated by the 'Tahiti' cultivar U.S. Plant Pat. No. 8,601). The new cultivar forms large true orange flowers with a fuchsia eye which display an iridescent appearance. The foliage is glossy and dark green in coloration with a red midvein. An attractive medium upright mounded growth habit is exhibited. The new cultivar can be readily distinguished from the parent 'Timor' cultivar U.S. Plant Pat. No. 9,144).

1 Drawing Sheet

SUMMARY OF THE INVENTION

The present invention comprises a new and distinctive Impatiens plant, botanically known as New Guinea Impatiens, and hereinafter is referred to by the cultivar name 'Orange Crush'.

The new cultivar is the product of a planned breeding program. More specifically, the breeding program which resulted in the production of the new cultivar was carried out in a controlled environment during 1993 at Arroyo Grande, Calif., U.S.A. The female parent (i.e., the seed parent) was a plant designated '305' (non-patented in the United States) which exhibits pink blossoms, and medium green foliage. The male parent (i.e., the pollen parent) was the 'Tahiti' cultivar (U.S. Plant Pat. No. 8,601) which exhibits light pink blooms with a red-purple eye, dark green foliage with a red midvein, and a compact growth habit. The parentage of the new cultivar can be summarized as follows:

'305'×'Tahiti'.

The seeds resulting from the above pollination were sown and plantlets were obtained which were physically and biologically different from each other. Selective study resulted in the identification of a single plant of the new cultivar. This plant initially was designated BFP-625.

It was found that the new cultivar of the present invention:

(a) exhibits attractive large orange flowers with a fuchsia eye,
(b) forms glossy dark green foliage,
(c) exhibits a good basal branching character, and
(d) exhibits a compact upright mounded growth habit.

The true orange blossoms are held gracefully above the shiny green foliage. Plants of the new cultivar can be grown close together in the greenhouse.

Asexual reproduction of the new cultivar by terminal or stem cuttings taken during 1993, at Arroyo Grande, Calif., U.S.A. has demonstrated that the characteristics of the new cultivar as herein described are firmly fixed and are retained through successive generations of such asexual propagation.

The 'Orange Crush' cultivar has not been observed under all possible environmental conditions to date. Accordingly, it is possible that the phenotype may vary somewhat with variations in the environment, such as temperature, light intensity, and day length.

When the new cultivar of the present invention is compared to the 'Timor' cultivar (U.S. Plant No. 9,144), it is found that the new variety exhibits a more compact growth habit and smaller foliage.

Plants of the new cultivar are marketed under the CELEBRETTE trademark by the Ball Horticultural Company.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at West Chicago, Ill., U.S.A.

DETAILED DESCRIPTION

The chart used in the identification of colors described herein is the R.H.S. Colour Chart of The Royal Horticultural Society, London, England. The plants were produced from cuttings taken from stock plants of the new cultivar and were transplanted during early November into 10 cm. (4 inch pots) and were grown in a soilless growth medium under standard greenhouse conditions at West Chicago, Ill., U.S.A. The greenhouse temperature was maintained at approximately 72° F. during the day and approximately 65° F. during the night. The plants were in flower eight to nine weeks later when the observations described hereafter were taken.

Propagation:

*Type cutting.*—Terminal tip.

*Time to initiate roots.*—Approximately 14 to 21 days with the shorter times generally being experienced in the summer and the longer times in the winter.

*Rooting habit.*—Fibrous, and branching.

Plant description:

*Form.*—Basal branching.

*Habit of growth.*—Compact upright mounded. A mature plant commonly measures approximately 6.5 to 7.5 cm. in height and approximately 15.5 to 16 cm. in width. This compares to a height of approximately 9.5 to 11 cm. and a width of approximately 16.5 to 17.5 cm. for the parent 'Timor' cultivar.

*Foliage.*—The configuration is elliptic with an acuminate apex and an acuminate base. The mature leaves of the new cultivar measure approximately 5.9 to 7.5 cm. in length×approximately 2.6 to 3.2 cm. in maximal width compared to approximately 9 to 10 cm. in length×approximately 3.3 to 4.5 cm. in maximal width for the 'Timor' cultivar. The leaf margins are serrate (as illustrated). The mature foliage of new cultivar is Yellow-Green Group 147A (adaxial), and Yellow-Green Group 147B with veins slightly lighter than Greyed-Purple Group 185A (abaxial). This compares to Yellow-Green Group 147A with a midvein of Greyed-Purple Group 183 (adaxial) and Greyed-Purple Group 191A with green veins (abaxial) for the 'Timor' cultivar.

Flower description:

*Flowering habit.*—Freely flowering.

*Natural flowering season.*—Throughout the year in a greenhouse environment.

*Flowers borne.*—Above foliage, arising from leaf axils.

*Flower color.*—Red Group 40A with the bases of the four lower petals being Red Group 53A forming an eye (adaxial) and Red Group 41B (abaxial). This compares to slightly darker than Orange-Red Group 33A (adaxial) and Orange-Red Group 32A (abaxial) for the 'Timor' cultivar.

*Quantity of flowers.*—Approximately 4 to 5 per axil. This can be compared to approximately 3 to 4 per axil for the 'Timor' cultivar.

*Number of petals.*—Five, and overlapping.

*Petal shape.*—Heart-shaped, with the three upper petals tending to have broader bases than the two lower petals.

*Flower size.*—Approximately 5.9 to 6.5 cm. in length and approximately 5.6 to 6.0 cm. in width. This can be compared to approximately 5.6 to 6.3 cm. in length and approximately 5.6 to 6.3 cm. in width for the parent 'Timor' cultivar.

*Flower buds.*—Ellipsoidal in configuration, and generally covered with three sepals plus two rudimentary sepals fused into the under surface of the superior petal. A spur originating from the base of the inferior sepal is approximately 4.9 to 5.2 cm. in length on fully opened flowers which can be compared to a length approximately 5 cm. for the spur of the 'Timor' cultivar. The spur coloration is Red Group 47A for both the new cultivar and the 'Timor' cultivar.

*Reproductive organs.*—The stamens are Red Group 43D. The anthers tend to be fused together forming one organ that surrounds the pistil. Commonly the anthers shed pollen prior to the stigma becoming receptive. The pollen coloration is Yellow-Orange Group 14B, and the ovary coloration is Yellow-Green Group 144A. This can be compared to a stamen coloration of Red Group 41D, a pollen coloration of Yellow Group 13C, and an ovary coloration of Green Group 143C for the 'Timor' cultivar.

I claim:

1. A new and distinct cultivar of New Guinea Impatiens named 'Orange Crush', substantially as herein shown and described, which:

(a) exhibits attractive large orange flowers with a fuchsia eye,
(b) forms glossy dark green foliage,
(c) exhibits a good basal branching character, and
(d) exhibits a compact upright mounded growth habit.

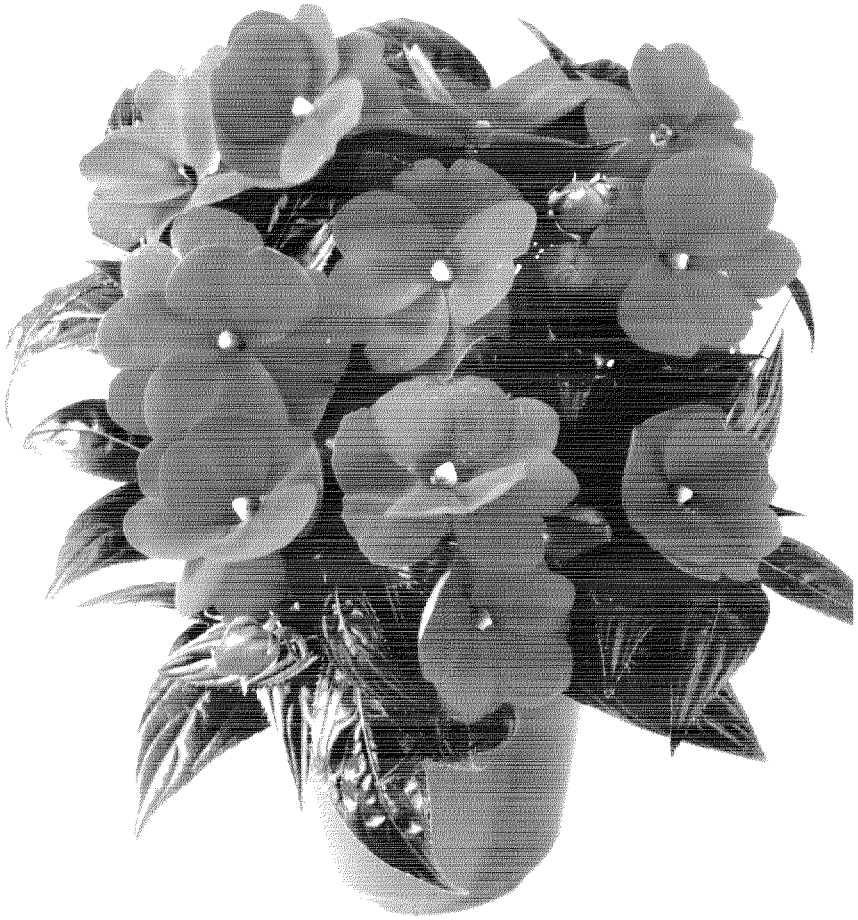

* * * * *